United States Patent [19]
Li

[11] Patent Number: 5,716,390
[45] Date of Patent: Feb. 10, 1998

[54] REDUCED DIAMETER ACTIVE FIXATION PACING LEAD USING CONCENTRIC INTERLEAVED COILS

[75] Inventor: Hong Li, Cupertino, Calif.

[73] Assignee: Pacesetter, Inc., Sylmar, Calif.

[21] Appl. No.: 695,042

[22] Filed: Aug. 9, 1996

[51] Int. Cl.⁶ ................................ A61N 1/05; A61N 1/04
[52] U.S. Cl. ........................ 607/127; 607/122; 607/126
[58] Field of Search ............................ 607/122, 126, 607/127, 128

[56] References Cited

U.S. PATENT DOCUMENTS

| | | | |
|---|---|---|---|
| 3,974,834 | 8/1976 | Kane | 607/127 |
| 4,000,745 | 1/1977 | Goldberg | 607/127 |
| 4,106,512 | 8/1978 | Bisping | 607/127 |
| 4,350,169 | 9/1982 | Dutcher | 607/127 |
| 4,463,765 | 8/1984 | Gold | 607/127 |
| 4,628,943 | 12/1986 | Miller | 607/127 |
| 4,886,074 | 12/1989 | Bisping | 607/122 |
| 5,003,992 | 4/1991 | Holleman et al. | 607/127 |
| 5,020,545 | 6/1991 | Soukup | 607/127 |
| 5,076,285 | 12/1991 | Hess et al. | 607/127 |
| 5,259,395 | 11/1993 | Li | 607/127 |
| 5,383,922 | 1/1995 | Zipes et al. | 607/122 |
| 5,425,755 | 6/1995 | Doan | 607/122 |
| 5,447,533 | 9/1995 | Vachon et al. | 607/120 |
| 5,476,501 | 12/1995 | Stewart et al. | 607/127 |
| 5,522,875 | 6/1996 | Gates et al. | 607/127 |

FOREIGN PATENT DOCUMENTS

| | | | |
|---|---|---|---|
| 491979 | 7/1992 | European Pat. Off. | A61N 1/05 |
| 2494118 | 5/1982 | France | A61N 1/04 |

*Primary Examiner*—Marvin M. Lateef
*Assistant Examiner*—Carl H. Layno

[57] ABSTRACT

A body implantable flexible lead assembly, adapted to transmit electrical pulses between a proximal end of the lead assembly and a distal end of the assembly to stimulate selected body tissue, includes a tubular, insulating housing connecting the proximal and distal ends of the assembly and having a central, longitudinal axis. At least two coiled, insulated conductors extend between the proximal and distal ends of the assembly for transmitting electrical signals, the coils of the at least two insulated conductors having substantially the same diameter. One of the coiled conductors is rotatable about the longitudinal axis relative to the other coiled conductor(s) and has a proximal end and a distal end. Last, a helix electrode is electrically connected to the distal end of the one coiled conductor for piercing the tissue to be stimulated, the one coiled conductor being adapted to extend or retract the helix electrode relative to the distal end of the assembly through rotation of the proximal end of the one coiled conductor.

6 Claims, 2 Drawing Sheets

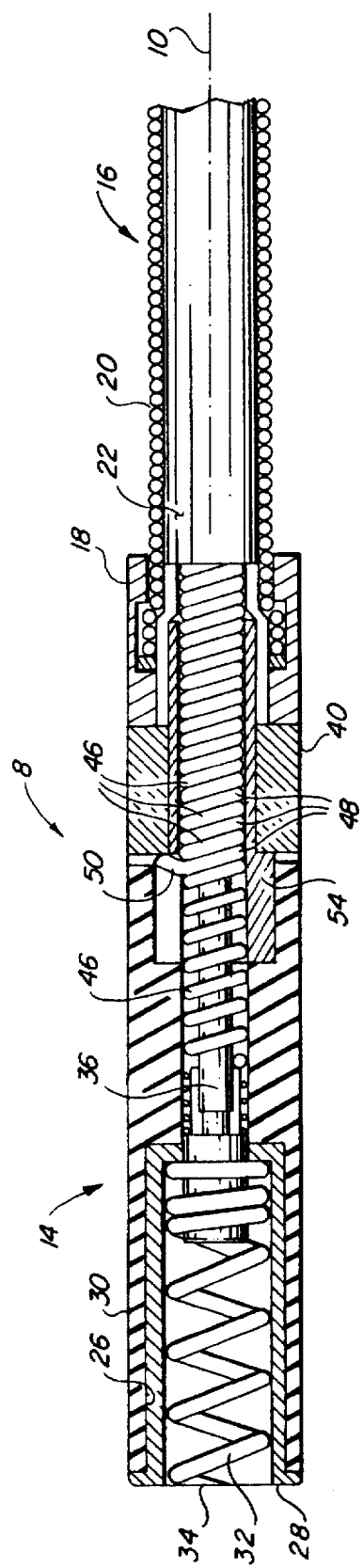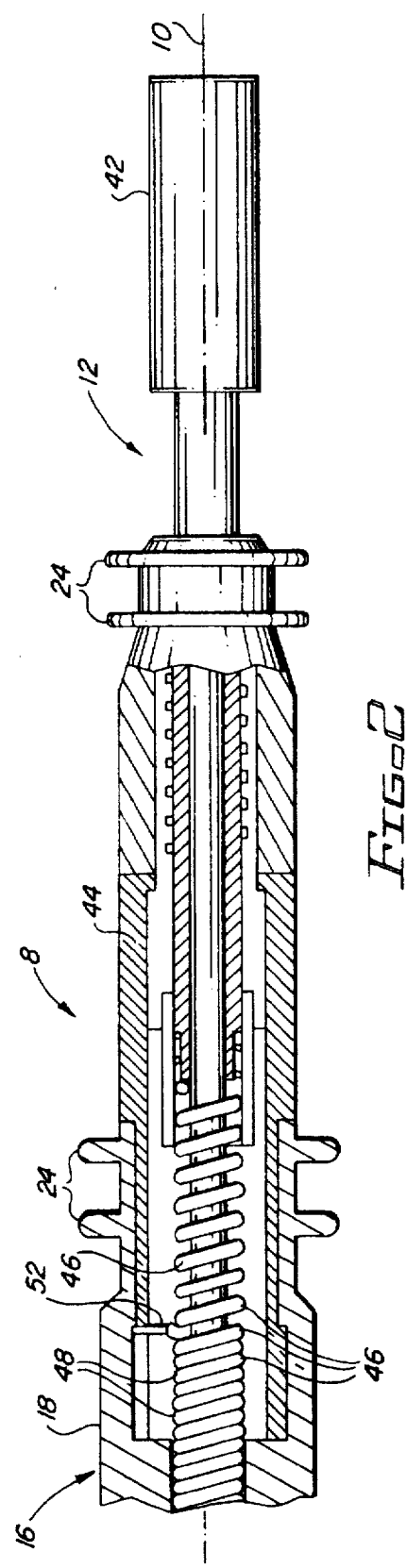

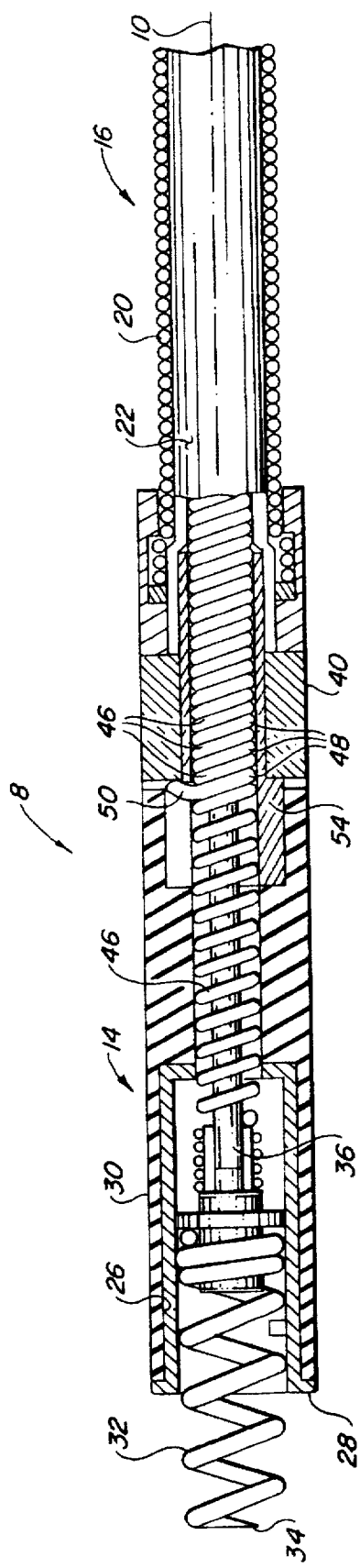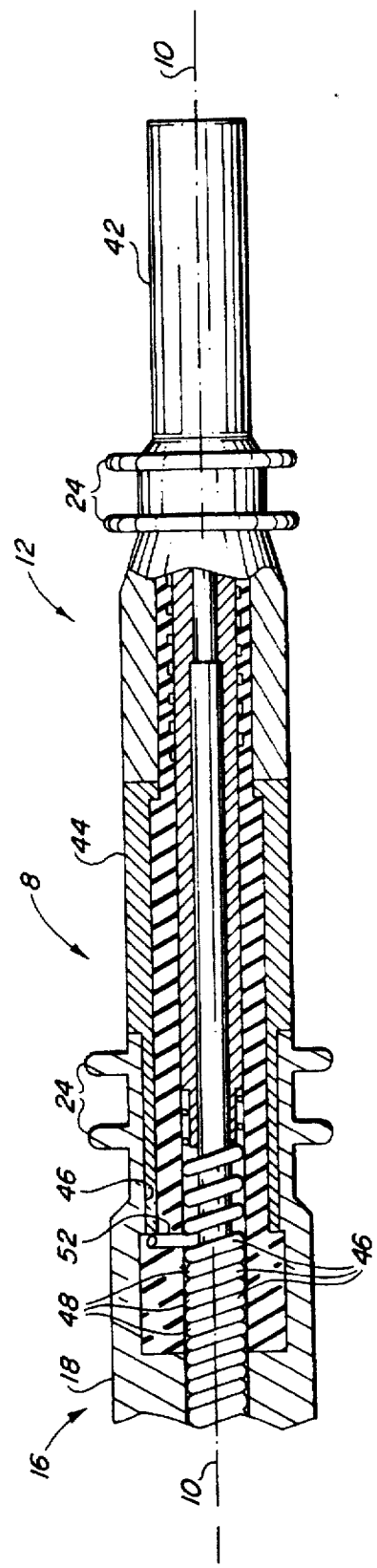

REDUCED DIAMETER ACTIVE FIXATION PACING LEAD USING CONCENTRIC INTERLEAVED COILS

FIELD OF THE INVENTION

The present invention relates generally to implantable medical devices for providing stimulating pulses to selected body tissue, and more particularly, to pacing lead assemblies of the active fixation type for connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart and representing cardiac activity, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to intimately contact the endocardium, the tissue lining the inside of the heart. The lead further includes a proximal end having a connector pin adapted to be received by a mating socket in the pacemaker. A flexible, coiled conductor surrounded by an insulating tube or sheath couples the connector pin at the proximal end and the electrode at the distal end.

To prevent displacement or dislodgment of the electrode and to maintain the necessary stable electrical contact between the lead tip and the endocardial tissue, the electrode must be firmly anchored relative to the tissue. To achieve this, the electrode of one known type of pacing lead, called an active fixation lead, may comprise, in accordance with one form thereof, a pointed helix adapted to be screwed into the heart tissue to be stimulated. Rotational torque applied to the connector pin at the proximal end of the lead is transmitted via the flexible, coiled conductor to the helical electrode which is thereby screwed into the heart tissue. In this fashion, the position of the electrode tip is mechanically stabilized, that is, the tip is positively anchored so as to remain securely in place during the lifetime of the implant. Removal of the screw-in electrode from the endocardium can be effected by counter-rotation of the connector pin. Thus, in a rotatable pin, screw-in type, active fixation lead, the conductor coil is used not only as an electrical conductor for coupling the connector pin and the helix electrode, but also as a tool for extending or retracting the helix electrode relative to the distal tip of the lead during lead myocardium fixation by rotating the connector pin.

As is known, many of today's intravascular endocardial leads are multipolar leads which include, besides an electrode at the tip, one or more ring electrodes proximally spaced behind the tip electrode for transmitting electrical stimulation pulses from the pulse generator to the heart and/or to transmit naturally occurring sensed electrical signals from the heart to the pulse generator. Thus, by way of example, in a typical bipolar lead having a helix tip electrode and a ring electrode, two concentric conductor coils which are either individually insulated or electrically isolated from each other by insulation disposed between the concentric coils, are carried within the insulative sheath. One of the conductor coils, typically the inner coil, connects the pulse generator with the helix electrode at the distal end of the lead while the other (typically outer) conductor coil connects the pulse generator with the ring electrode positioned behind the distal end of the lead. Normally, the helical tip electrode is the negative or stimulating electrode, while the ring electrode serves as the anode for pacing and also as an electrode for sensing intrinsic heart activity.

One of the drawbacks of existing screw-in type multipolar pacing leads is their large overall lead body diameter resulting from the use of concentric conductor coils. It is desirable to minimize the lead body diameter to facilitate passage of the lead through small diameter blood veins so as to minimize the resistance to insertion and removal of the lead. It is also desirable to minimize lead body diameter so as to reduce the diameter of the introducer sleeve where implantation is effected by means of a lead introducer. Since the purpose of the introducer is to provide direct entry of the endocardial lead into a vessel, it is important to minimize the size of the opening in the vessel to minimize trauma at the introduction site.

In the case of multipolar passive pacing leads, it is known that the outside diameter of the lead body may be reduced by insulating the individual conductors and winding all of the conductor coils in interleaved fashion on the same diameter. See, for example, A. Lindgren & S. Jansson, *Heart Physiology and Stimulation* 166 (1992) and copending U.S. patent application Ser. No. 08/504,207, filed Jul. 19, 1995, entitled "Endocardial Lead With Reduced Diameter Tip Portion and Method For Making Such Lead". Further, U.S. Pat. No. 4,106,512, issued Aug. 15, 1978, discloses in FIG. 3 thereof an active fixation, screw-in type pacing lead in which the helix tip electrode comprises a forwardly projecting extension of a closely wound inner coiled wire conductor. The axial motion of the helix electrode is achieved by turning the inner conductor in sliding contact with a certain length of the inner surface of the turns of an outer, coaxial conductor which is similarly closely wound into a coil having a larger diameter than the inner coiled conductor. In this fashion, a screwing effect is made possible. The external coiled conductor is stationary and terminates at a ring electrode at the distal end of the lead so that the tissue may be stimulated by means of the ring electrode before the helix electrode is screwed into the tissue. In this connection, the inner and outer coiled conductors are not insulated from each other along the portions of the two conductors that are in contact with each other.

Another drawback of today's active fixation screw-in type pacing leads is that the inner, "torque transfer" coil that is attached to the helix electrode must often be rotated many times (up to ten turns or more) to effect helix fixation or retraction. This is not only inconvenient and time consuming, but may cause lead perforation due to the buildup of torque on the lead body. In existing active fixation screw-in leads, the number of connector pin turns is a function of several factors such as the length of the lead body (a longer lead requires more turns of the connector pin to advance or retract the helix electrode a given distance) and the friction between the conductor coil and the surrounding surfaces.

Yet another disadvantage of existing screw-in type active fixation leads is that the distal end portion of the lead (also sometimes referred to as the electrode head) is relatively rigid and long, for example, up to 0.67-inch in length. These characteristics increase not only the difficulty of implantation and positioning the lead tip but also the possibility of perforation or dislodgment due to heart movement. A conventional bipolar active fixation lead requires a rigid structure and critical alignment between the distal tip and the ring electrode to assure a smooth transfer of force from the rotating inner conductor to the helix assembly. In the conventional design, the conversion from rotational to linear motion occurs at the distal end of the inner coil conductor which acts as a long spring. Since torque is applied at the proximal end of this long spring, excessive drag in the distal mechanism can store some of this force in the form of compression. Thus, the number of turns required to extend the helix may become excessive and unwanted lead movement may occur if the compression is suddenly released.

Accordingly, an overall object of the present invention is to reduce the outer diameter and therefore the cross sectional area of multipolar endocardial leads employing active fixation means.

It is also an object of the invention to reduce the number of revolutions of the lead connector pin required to fully extend or retract the helix electrode during lead fixation or extraction.

It is yet another object of the invention to reduce the length and rigidity of the distal end portion of active fixation leads of the type employing screw-in type electrodes.

SUMMARY OF THE INVENTION

In accordance with a preferred, exemplary embodiment of the present invention, there is provided a body implantable flexible lead assembly adapted to transmit electrical pulses between a proximal end of the lead assembly and a distal end of the assembly to stimulate selected body tissue. The assembly includes a tubular, insulating housing connecting the proximal and distal ends of the assembly and having a central, longitudinal axis. A pair of coiled, insulated conductors extend between the proximal and distal ends of the assembly for transmitting electrical signals, the coils of the pair of insulated conductors having substantially the same diameter. One of the coiled conductors is rotatable about the longitudinal axis relative to the other coiled conductor and has a proximal end and a distal end. Last, a helix electrode is electrically connected to the distal end of the one coiled conductor for piercing the tissue to be stimulated, the one coiled conductor being adapted to extend or retract the helix electrode relative to the distal end of the assembly through rotation of the proximal end of the one coiled conductor.

Because the coiled conductors are wound on the same diameter rather than coaxially on different diameters, the overall diameter of the lead assembly of the present invention can be substantially reduced. Moreover, because during rotation the helix coil is guided by the stationary coil much like a threaded machine screw relative to a stationary nut, the helix is fully extendable and retractable with a minimum number of turns of the connector pin.

Further in accordance with the present invention, the distal portion of the lead may be made both more flexible and shorter. Decreasing rigidity at the distal portion of the lead reduces the possibility of perforation or dislodgment due to heart movement. Since linear movement occurs throughout the length of the lead through rotation of the one conductor coil supported along its length by the stationary conductor coil, the section between the distal tip and the ring electrode can be deflected to some degree without interfering with helix extension or retraction. Thus, the distal assembly can be made more flexible by using a material such as silicone rubber between the distal tip and the ring electrode.

The distal portion can be made shorter since only a single support is needed at the transition from the stationary coil, as compared to the dual bushings now required. A shorter distal section decreases the "leverage" with which movement is transferred to the tip and thus reduces the possibility of "micro dislodgment", where the lead does not fully dislodge but the tip loses intimate contact with the endocardial tissue and excessive stimulation voltage is required of the pacing system.

BRIEF DESCRIPTION OF THE DRAWINGS

Further objects, features and advantages of the invention will become apparent from the "Detailed Description of the Preferred Embodiments", below, when read in conjunction with the accompanying drawings, in which:

FIG. 1 is a longitudinal section of the distal end portion of an active fixation lead assembly in accordance with the present invention, the helix electrode of the assembly being shown in its fully retracted position;

FIG. 2 is a longitudinal section of the proximal end portion of the lead assembly in the fully retracted configuration shown in FIG. 1;

FIG. 3 is a longitudinal section of the distal end portion of the lead assembly of FIG. 1, the helix electrode of the assembly being shown in an extended position; and FIG. 4 is a longitudinal section of the proximal end portion of the lead assembly in the extended configuration shown in FIG. 3.

DETAILED DESCRIPTION OF THE PREFERRED EMBODIMENTS

The following description presents a preferred embodiment of the invention representing the best mode contemplated for practicing the invention. This description is not to be taken in a limiting sense but is made merely for the purpose of describing the general principles of the invention whose scope is defined by the appended claims. Moreover, the context in which the invention is shown herein, that is, a bipolar pacing and sensing lead, is illustrative only; it will be understood by those skilled in the art that the invention may be used in a wide variety of multipolar body implantable pacing leads of the active fixation type employing a screw-in electrode.

Referring now to the drawings, there is shown a bipolar, endocardial active fixation pacing and sensing lead assembly 8 having a longitudinal axis 10, a proximal end portion 12, a distal end portion 14 and an intermediate portion 16 connecting the end portions 12 and 14. The entire length of the intermediate portion 16 of the lead assembly 8 may be encased within a tubular, insulating housing or sheath 18 made of an insulating biocompatible, biostable material such as polyurethane or silicone rubber. Alternatively, as shown in FIGS. 1 and 3, part of the length of the sheath 18 adjacent the distal end portion 14 may be omitted to accommodate an exposed defibrillator coil 20 wound about an outer insulating tubular layer 22 and connected to the pacemaker and/or a defibrillator, all as well known in the art. The proximal end portion 12 is adapted to be plugged into the socket or receptacle of a cardiac pacemaker (not shown) and for this purpose the tubular housing 18 includes longitudinally spaced sets of annular ribs 24 for sealing the pacemaker receptacle against the entry of bodily fluids.

The distal end portion 14 of the lead 8 includes a metallic, tubular housing 26 including an open tip 28. The tubular housing 26 is enclosed within an insulating layer 30. The distal end portion 14 of the lead 8 further includes a rotatable, extendable/retractable helix electrode 32 shown in FIG. 1 fully retracted within the tubular housing 26. As is well known, the helix electrode 32 serves both as a fixation means to securely anchor the distal end of the lead relative to the tissue to be stimulated and as an electrically conductive contact element for transmitting electrical stimulation and sensed pulses. The helix electrode 32, which may be made of a platinum-iridium alloy, for example, has a sharp end 34 adapted to pierce the endocardial tissue. The helix electrode 32 is carried by a shaft 36 welded or otherwise secured to the proximal end of the electrode 32.

In the particular embodiment under consideration, the distal end portion 14 further includes a ring electrode 40 which is the anode portion of the circuit for pacing and for sensing the heart's intrinsic activity. The sensed signals provide information to the pacemaker and may be used to trigger stimulation impulses.

The proximal end portion 12 of the lead assembly 8 includes an electrical connector pin 42 and an electrically conductive contact ring 44. As is well known, the pin 42 and the contact ring 44 engage corresponding terminals in a receptacle within the cardiac pacemaker. The connector pin 42 on the proximal end portion 12 is hollow and is electrically coupled to the helix electrode shaft 36 by means of a rotatable coil conductor 46 (also referred to as the first coil) enclosed within the tubular housing 18. The contact ring 44 on the proximal end portion 12 is electrically coupled to the ring electrode 40 by a stationary coil conductor 48 (also referred to as the second coil) within the sheath 18. Specifically, the coil conductor 48 has a distal extremity 50 welded or otherwise secured to the ring electrode 40 and a proximal extremity 52 likewise secured to the contact ring 44. A support 54 under the ring electrode 40 is used to support the coil conductors at the point where the rotatable coil conductor 46 exits the distal extremity of the stationary coil conductor 48. The support 54 may be made of titanium and anodized so that it serves to isolate the ring electrode 40 from short circuit due to fluid entering the open tip 28 of the lead.

In a manner well known in the art, the coil conductors 46 and 48 are provided with insulative coatings permitting them to be wound in interleaved fashion on substantially the same diameter, as shown in the drawings. It will thus be seen that given the helical sense of the helix electrode 32 and the coils of the associated conductor coil 46, as illustrated in FIG. 1, rotation of the connector pin 42 in a clockwise direction (as viewed from the proximal end of the lead) will cause advancement of the helix electrode 32 and its extension from the open tip 28 of the tubular housing 26 to an extended position (FIG. 3), while rotation of the connector pin 42 in a counterclockwise direction will result in retraction of the electrode 32 to its fully retracted position shown in FIG. 1. The stationary coil 48 acts as a guide for the movable coil 46, analogous to a threaded screw fastener in which the screw is positively advanced relative to an associated, stationary nut. Accordingly, once the situs of lead fixation has been determined, fixation may be effected expeditiously with a minimum number of turns of the connector pin 42.

As is well known in the art, each of the coil conductors 46 and 48 may comprise a multifilar conductor for redundancy to provide continued stimulation and sensing in the event one of the conductor strands breaks. Moreover, the invention may be applied to rate modulated systems employing sensors for detecting the body's need for cardiac output. In that case, stationary conductor coils in addition to the stationary coil conductor 48, may be wound on the same diameter and interleaved with the coil conductors 46 and 48.

In accordance with well-known implantation procedures, a style (not shown) is passed through the hollow connector pin 42 and the central cavity or lumen of the associated coil conductors 46 and 48 to enable the implanting surgeon to orient the distal end portion 14 of the lead and to position the helix electrode 32 under fluoroscopy to a desired location in the heart.

It will be understood that with the termination of the coil conductor 48 at the ring electrode 40, there will remain gaps between adjacent turns of the portion of the insulatively coated conductor 46 extending beyond the coil conductor 48, providing increased flexibility.

Further, with this invention, linear movement occurs throughout the length of the lead through rotation of the rotatable coil conductor 46 supported along its length by the stationary coil conductor 48. Therefore, the section of the lead between the distal tip 28 and the ring electrode 40 can be deflected to some degree without interfering with helix extension or retraction. Thus, the distal assembly can be made more flexible by using a material such as silicone rubber between the distal tip 28 and the ring electrode 40. The distal portion 14 of the lead can also be made shorter, since only a single support 54 is needed, at the transition from the stationary coil, as compared to the dual bushings needed in present active fixation leads.

It should be appreciated that the foregoing description is only illustrative of the invention. Various alternatives and modifications can be devised by those skilled in the art without departing from the spirit of the invention. Accordingly, the present invention is intended to embrace all such alternatives, modifications and variations as fall within the scope of the appended claims.

What is claimed is:

1. A body implantable flexible lead assembly adapted to transmit electrical pulses between a proximal end of the lead assembly and a distal end of the assembly to stimulate selected body tissue, the assembly including:

a tubular, insulating housing connecting the proximal and distal ends of the assembly and having a central longitudinal axis;

a pair of coiled, insulated conductors extending between the proximal and distal ends of the assembly for transmitting electrical signals, the coils of the pair of insulated conductors having substantially the same diameter, portions of the pair of coiled conductors being interleaved, one of the coiled conductors being rotatable about the longitudinal axis relative to the other coiled conductor and having a proximal end and a distal end; and a helix electrode electrically connected to the distal end of the one coiled conductor for piercing the tissue to be stimulated, the one coiled conductor being adapted to extend or retract the helix electrode relative to the distal end of the assembly through rotation of the proximal end of the one coiled conductor.

2. A lead assembly, as defined in claim 1, in which the coils of the pair of coiled conductors are contiguous along a portion of the conductors intermediate the proximal and distal ends of the assembly.

3. A lead assembly, as defined in claim 1, including an electrically conductive contact adjacent the proximal end of the assembly and a sensing electrode adjacent the distal end of the assembly, the other of the pair of coiled conductors electrically connecting the conductive contact and the sensing electrode.

4. A lead assembly, as defined in claim 1, in which:

the insulating housing includes an outer surface; and the lead assembly includes a defribillator coil mounted on the outer surface of the housing and extending proximally from the distal end of the assembly.

5. A lead assembly, as defined in claim 1, in which the other of the pair of coil conductors has a distal extremity;

the lead assembly further including:

a coil support at the distal extremity of the other of the pair of coiled conductors.

6. A lead assembly, as defined in claim 5, in which the coil support comprises anodizetitanium.

* * * * *